United States Patent [19]

Reich

[11] Patent Number: 4,517,133

[45] Date of Patent: May 14, 1985

[54] METHOD OF PREPARING SULFONYL ISOCYANATES

[75] Inventor: Karl Reich, Carlsberg, Austria

[73] Assignee: Teroson GmbH, Heidelberg, Fed. Rep. of Germany

[21] Appl. No.: 534,029

[22] Filed: Sep. 20, 1983

[30] Foreign Application Priority Data

Sep. 22, 1982 [DE] Fed. Rep. of Germany ....... 3235045

[51] Int. Cl.$^3$ ........................................... C07C 153/00
[52] U.S. Cl. ................................................ 260/545 R
[58] Field of Search .................................... 260/545 R

[56] References Cited

U.S. PATENT DOCUMENTS 2,974,164  3/1961  Franz ............................. 260/545 R

FOREIGN PATENT DOCUMENTS 0079004  5/1983  European Pat. Off. ........ 260/545 R

Primary Examiner—Alan Siegel
Attorney, Agent, or Firm—P. M. Pippenger

[57] ABSTRACT

Sulfonyl isocyanates having the formula R—SO$_2$—NCO (wherein R is a C$_1$- to C$_{18}$- alkyl radical, a phenyl radical, a C$_1$- to C$_{18}$- alkyl phenyl radical or an isocayanate group) are obtained in high yield and excellent purity by reaction of the corresponding sulfonyl chlorides R—SO$_2$—Cl with trimethyl silyl isocynate in the presence of catalytic amounts of Lewis acids. The preferred Lewis acids are halides having the formula AX$_n$ (A=B, Al, Ti, Sn, V, Sb, Fe or Zn; n=valence of A).

6 Claims, No Drawings

METHOD OF PREPARING SULFONYL ISOCYANATES

BACKGROUND OF THE INVENTION

1. Field of the Invention

The present invention is concerned with the preparation of sulfonyl isocyanates having the general formula $$R-SO_2-NCO \quad \quad I$$

wherein an isocyanate group is linked directly to the $SO_2$ group and R is a $C_1$- to $C_{18}$-alkyl, a phenyl, a $C_1$- to $C_{18}$-alkyl phenyl radical or an isocyanate group.

2. Discussion of the Prior Art

Compounds having the formula I became of importance with respect to the stabilization of organic isocyanates against decomposition and discoloration (see U.S. Pat. No. 33,330,849, DE-Pat. No. 2 030 316), and the stability increase of polyurethane prepolymers (DE-Pat. No. 1 245 590). Furthermore sulfonyl diisocyanate forms an intermediate compound for producing diacyl sulfamides which are used for stabilization and acceleration of reactive acrylate adhesives (German patent application No. P 31 37 306.2-43).

Although sulfonyl isocyanates are already known since the beginning of this century, systematic studies of this class of substances started only 50 years later. For one reason this results from the difficulty of obtaining these compounds synthetically and for another from their high reactivity. A summary of the methods of forming these compounds known in 1964 is given by H. Ulrich in Chem. Rev. 65 (3), 369–376 (1965). From the voluminous recent literature the following important general methods of obtaining sulfonyl isocyanates are available:

1. Methods of preparing aliphatic sulfonylisocyanates 1.1. Reaction of sulfonylchlorides and anhydrides with silver isocyanate:

$$CH_3-SO_2-Cl + AgNCO \rightarrow CH_3-SO_2-NCO + AgCl$$

O. C. Billeter, Ber. 38, 2013–2015 (1905); L. Field, P. H. Settlage, J.Am.Chem.Soc. 76, 1222–1225 (1954).

1.2 Elimination of alcohols from sulfonylurethanes or their silylated analogues:

$$CH_3-SO_2-NCO + C_2H_5OH$$

H. R. Davis, US-PS 3 185 677;
W. H. Daly, H. J. Holle, J. Org. Chem. 39(11), 1597–1600 (1974).

1.3 Heterogeneous reaction of sulfochlorides with alkali metal cyanates:

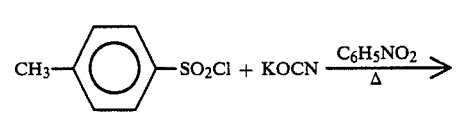

$$CH_3-SO_2-NCO + KCl$$

Y. Nadachi, M. Kokura, Japan. Kokai 76-26 816.

2. Methods of preparing aromatic sulfonylisocyanates.

2.1. Reaction of sulfonamides with phosgene in high boiling inert solvents:

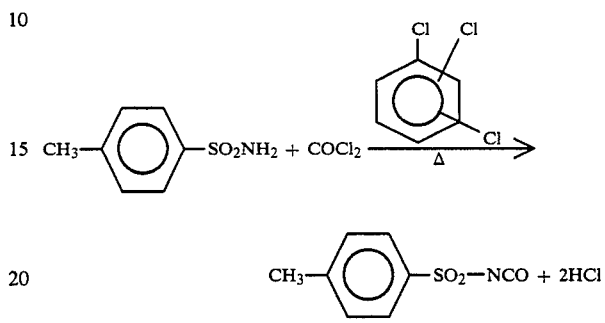

K. Krzikalla, DE-PS 817 602.

2.2 Reaction of N-alkyl-N'-arylsulfonylureas, which are intermediates from the reaction of sulfonamides with alkyl isocyanates, with phosgene:

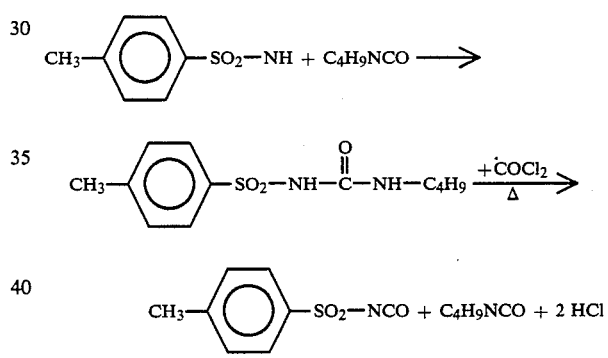

H. Ulrich, B. Tucker, A. A. R. Sayigh, J. Org, Chem. 31 (8), 2658–2661 (1966) and Angew. Chem. 78 (16), 761–769 (1966);
H. Ulrich, US-PS 3 330 849;
A Adnan, A. A. R. Sayigh, W. Ulrich, US-PS 3 352 909;
H. Ulrich, US-PS 3 379 758;
A. A. R. Sayigh, H. Ulrich, US-PS 3 371 114,
US-PS 3 484 466.

2.3 Reaction of aromatic sulfonylchlorides with alkali metal cyanates:

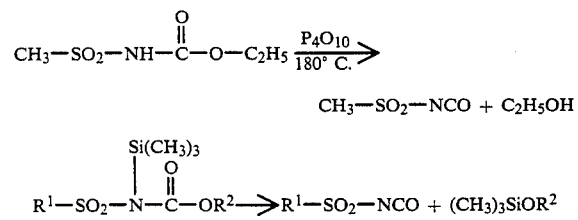

J. E. Franz, US-PS 2 974 164.

2.4 Reaction of aromatic hydrocarbons with chlorosulfonylisocyanate:

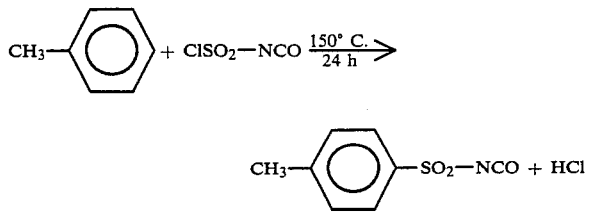

H. Bestian, W. Blau, D. Gunther, DE-PS 1 289 526.

3. Methods of forming sulfonyldiisocyanate
 3.1 Reaction of bromocyanogen with $SO_3$:

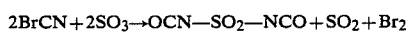

R. Graf, DE-PS 940 351.
 3.2 Thermal or catalytic decomposition of chlorosulfonylisocyanate:

$$OCN-SO_2-NCO + Cl_2 + SO_2$$

K. Matterstock, R. Graf, DE-PS 1 152 093.

3.3 Reaction of chlorosulfonylisocyanate with silver isocyanate:

R. Appel, H. Gerber, Ber. 91, 1200 (1958).

All of the above mentioned processes suffer from substantial disadvantages. The use of silverisocyanate for instance is impeded by the high price and the laborious, time-consuming and expensive regeneration of the substance while when using potassium cyanate only a small yield is obtained from the heterogeneous reaction. It is impossible to obtain a homogeneous reaction by use of a suitable solvent since the strong reactivity of the sulfonylisocyanate results, especially under the influence of high temperature, in a yield-reducing reaction of the same with the solvents in question. In reactions using phosgene it is disadvantageous that the substance is highly poisonous and thus a health hazard; furthermore the by-products have to be removed. In elimination reactions from sulfonylurethanes it is an unfavourable fact that these starting materials first have to be specially synthesized and subsequently it is not possible to regenerate the elimination products in the conversion reaction itself.

In the methods of preparing sulfonyldiisocyanate known in the art it is on the one hand the high toxicity of the rather expensive bromocyanogen which is interfering and on the other hand the fact that during the thermal decomposition of chlorosulfonylisocyanate only one moiety of the starting material is utilized, while the other moiety forms chlorine and sulfurdioxide which again require special exhaust gas treatment.

SUMMARY OF THE INVENTION

It is the object of the present invention to find a reaction by which aliphatic and aromatic sulfonyl isocyanates as well as sulfonyldiisocyanates are obtained in a simple manner with high yield and purity while avoiding the mentioned disadvantages. Unexpectedly it was found that the above disadvantages are avoided when sulfonylhalides are reacted with trimethylsilylisocyanates in the presence of suitable catalysts as for instance Lewis acids, and that especially sulfonyldiisocyanate and aromatic sulfonyl isocyanates but also aliphatic sulfonyl isocyanates are obtained with higher yield and purity, according to the following equation wherein R has the same meaning as set forth above:

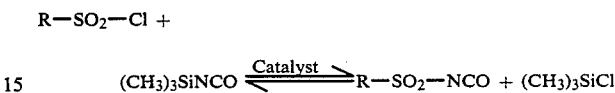

The use of trimethyl silylisocyanate has indeed been proposed by W. Buss, H. J. Krannich and W. Sundermeyer in Ber. 109, 1486–1490 (1976) for introduction of an isocyanate group into trimethyl silyloxysulfonylchloride. But when reacting chlorosulfonylisocyanate, which is the most reactive sulfonylisocyanate of the above series, with trimethyl silylisocyanate under the given conditions, it is impossible to isolate the desired sulfonyldiisocyanate but only traces of this substance are detectable by gas chromatography. On the other hand an extraordinarily smooth reaction is obtained wherein sulfonyldiisocyanate for instance is formed with high purity and a yield of 80% by adding the catalysts of the invention.

The present invention is thus directed to a new method of forming sulfonylisocyanates having the general formula $$R-SO_2-NCO, \qquad I$$

wherein R is a linear or branched $C_1$- to $C_{18}$-alkyl radical, a phenyl radical, an alkyl phenyl radical having at least one linear or branched alkyl group containing from 1 to 18 C-atoms, or an isocyanate group, by reacting the corresponding sulfonylchloride having the formula

wherein R has the meaning set forth above, with an isocyanate. The process is characterized in that trimethyl silylisocyanate is used as the isocyanate and that the reaction is carried out in the presence of catalytic amounts of Lewis acids.

It is one advantage of the conversion reaction of the present invention that merely a suitable rectification apparatus with packed columns is needed. The expensive high temperature reactors necessary for thermic decomposition of chlorosulfonylisocyanate to obtain sulfonyldiisocyanate can thus be dispensed with.

It is a further important economic advantage of the present method, that a favourable space-time-yield is obtained by the high reaction rate which results from the homogeneous reaction. On the other hand it is possible to re-use the chlorotrimethyl silane which is recovered from the reaction nearly quantitatively, for producing again trimethyl silylisocyanate so that the following over all reaction equation results, which is not obtainable through a direct path since the direct conversion would be a heterogeneous reaction:

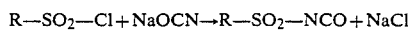

DETAILED DESCRIPTION OF THE INVENTION

The organic sulfonylchlorides required as a starting material can easily be formed from the corresponding sulfonic acids. As described by L. Graf in DE-Pat. No. 928 896 chlorosulfonylisocyanate is easily available from chlorocyanogen and sulphur trioxide.

Trimethyl silylisocyanate can advantageously be prepared according to DE-Pat. No. 1 965 741 with 89% yield by reacting chlorotrimethyl silane with sodium cyanate using dimethyl formamide as a solvent.

By selection of a suitable catalyst and the reaction temperature the course of the conversion can be substantially influenced.

A great many metal and non-metal halides, which generally can be considered Lewis acids are useful for catalyzing the reaction of the invention, especially the halides, i.e. the fluorides, bromides, iodides and especially the chlorides of boron, aluminum, titanium, tin, vanadium, antimony, iron and zinc, having the general formula $AX_n$ (n=valence of A). Each of the mentioned compounds can be used alone or as a mixture. Within the scope of the invention titanium and tin halides as for instance titanium tetrachloride or tin tetrachloride are especially suitable, whereby in the case of the reactive chloro sulfonylisocyanates better results are obtained with tin tetrachloride while for preparation of aromatic or aliphatic sulfonylisocyanates titanium tetra-chloride or combinations of tin and titanium tetra-chloride are preferred.

The amount of catalyst is about 0.1 to 20% by weight preferably about 5 to 10% by weight, based on the amount of trimethyl silylisocyanate used.

Although the exact principle of the catalytic action cannot yet be explained, some observations point to a complex first being formed between the catalyst and the trimethyl silylisocyanate, resulting in the formation of a small amount of chlorotrimethyl silane. Presumably this intermediate compound reacts with the sulfochloride, by which reaction the NCO-groups are transferred and the catalyst is regenerated.

It is also possible to influence the reaction considerably by temperature control. Although the reaction can be started by heating the mixture of all components, it became evident, that especially in the case of the less reactive sulfonylchlorides it is more favourable to add the trimethyl silylisocyanate during the course of the reaction in such a manner that a bottom temperature of 120° to 130° C. can be maintained and the temperature does not rise above 160° C. subsequently.

The sulfonylisocyanates obtained by the method of the invention were separated by subsequent rectification of the reaction mixture, using vacuum if necessary. The sulfonylisocyanates were definitively characterized by reaction with benzyl alcohol and the structure of the resulting addition compounds obtained in quantitative yield was proven by IR-, $^{13}$C-NMR- and $^1$H-NMR-spectra.

The following examples are given for illustration of the invention.

EXAMPLE 1

Preparation of sulfonyldiisocyanate 28,30 g of chlorosulfonylisocyanate (0,200 mol) and 23,04 g of trimethyl silylisocyanate (0,200 mol) where heated to reflux temperature by means of an oil bath with stirring within a round flask equipped with a packed column. 1.0 ml of tin tetrachloride were added to the boiling mixture, whereupon a quick temperature drop at the column head from 91° to 58° C. was observed. The head product (chlorotrimethyl silane) was removed in such a manner, that a still temperature of 58° to 60° C. could be maintained. After a reaction time of 2,5 h the bottom temperature had increased from 97° to 143° C. while in spite of infinite reflux the still temperature did not drop beneath 126° C. By rectification of the reaction mixture over a Vigreux-column under vacuum 23,74 g of pure sulfonyldiisocyanate (80% of theory), bp. (18 mbar) 46° to 47° C., a colorless liquid, were obtained.

According to GC-analysis the distillation product obtained during the reaction (26,00 g of colorless liquid) consisted of 82% chlorotrimethyl silane and 18% trimethyl silylisocyanate; thus 21,32 g or 98% of the theoretical amount of chloro trimethyl silane were recovered.

Characterisation of the sulfonyldiisocyanate 5,41 g of anhydrous benzyl alcohol (0,050 mol) were dissolved in 200 ml of absolute benzene and 3,70 g of sulfonyldiisocyanate were added dropwise. As a result the reaction temperature increased and a colorless precipitate formed. The precipitate was suction filtered and dried (4.05 g, 99% of theoretical value). After re-crystallization from diethylether/petrol ether 7,61 g of N,N'-bis(benzyloxycarbonyl)-sulfamide, colorless crystals, m.p. (decomposition) 141° C., were obtained.

Structure:

$$\text{C}_6\text{H}_5-\text{CH}_2-\text{O}-\overset{\overset{\text{O}}{\|}}{\text{C}}-\text{NH}-\text{SO}_2-\text{NH}-\overset{\overset{\text{O}}{\|}}{\text{C}}-\text{O}-\text{CH}_2-\text{C}_6\text{H}_5$$

| | |
|---|---|
| IR-spectrum (KBr): | 3280/3200 cm$^{-1}$ ν(NH) |
| | 1750 cm$^{-1}$ ν(C═O) |
| | ν(SO$_2$)as + ν(SO$_2$)sy |
| | Assignment not definite |
| $^{13}$C—NMR-spectrum (acetone d$_6$) | 151,36 ppm C═O |
| | 136,38 ppm ⎫ |
| | 129,08 ppm ⎬ C$_6$H$_5$— |
| | 129,02 ppm ⎪ |
| | 128,64 ppm ⎭ |
| | 64,42 ppm —CH$_2$— |
| $^1$H—NMR-spectrum (acetone d$_6$) | 10,71 ppm, s, 2 H for —NH— |
| | 7,34 ppm, s, 10 H for —ArH |
| | 5,16 ppm, s, 4 H for —CH$_2$—. |

The IR-spectrum was completely identical to the spectrum of a substance synthesised from a sulfonyldiisocyanate (which was prepared according to K. Appel, H. Gerber, Ber. 91, 1200 (1958) from chlorosulfonylisocyanate and silverisocyanate) and benzyl alcohol.

EXAMPLE 2

Preparation of 4-methyl benzenesulfonylisocyanate 95,44 g of 4-methyl benzene sulfonylchloride (0,500 mol) were molten in an round flask, 2.5 ml of titanium tetrachloride were added—resulting in a brown color of the reaction mixture—and heated to 120° C. with a packed column mounted on the flask. Subsequently 61,13 g of trimethyl silylisocyanate (0,600 mol) were added dropwise in such a manner that the bottom temperature was maintained at 120° C. When the addition was started a yellow precipitate formed and at the same time the still temperature dropped to 58° C. Corresponding to example 1 the head product distilled at a temperature of 58° to 59° C. while the bottom temperature was gradually increased to 150° C. In this way 46,66 g of a colorless liquid, bp. 58° to 59° C., were distilled off within 3 hours (GC: pure chlorotrimethyl silane). The reaction mixture was distilled through a Claisen-bridge under oil pump vacuum, whereby 83,60 g of a slightly yellow liquid, bp. (1 mbar) 92° to 96° C., were obtained. By rectification of the same through a Vigreux-column 72,94 g (74% of theoretical value) of colorless 4-methyl benzene sulfonylisocyanate, bp. (0,9 mbar) 94° to 94,5° C., were obtained which according to GC-analysis still contained 8% 4-methyl-benzene-sulfonyl-chloride.

Characterisation of 4-methyl-benzenesulfonylisocyanate

To 2,74 g of anhydrous benzyl alcohol (0,025 mol) in 50 ml of absolute benzene 5.00 g of 4-methyl benzenesulfonylisocyanate were added dropwise. The temperature of the reaction mixture increased and a clear solution was obtained. By evaporation of the benzene solution, addition of some petroleum ether and suction filtering 7,05 g of colorless crystals were obtained. After recristallisation from benzene/petrol ether 6,20 g of N-benzyl oxycarbonyl4-methyl benzosulfonamide, colorless crystals, m.p. 100° to 101° C., homogeneous in thin layer chromatography (silica gel, benzene/diethyl ether) were obtained.

Structure:

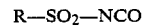

| IR-spectrum (KBr) | 3290 cm$^{-1}$ $\nu$(NH) |
| --- | --- |
| | 1740 cm$^{-1}$ $\nu$(C=O) |
| | 1350 cm$^{-1}$ $\nu$(SO$_2$)as |
| | 1160/1170 cm$^{-1}$ $\nu$(SO$_2$)s |
| $^{13}$C—NMR-spectrum (CDCl$_3$) | 150,77 ppm (=O) |
| | 144,86 ppm ⎫ |
| | 135,91 ppm ⎪ |
| | 134,68 ppm ⎬ —C$_6$H$_4$—/C$_6$H$_5$— |
| | 129,53 ppm ⎪ |
| | 128,53 ppm ⎪ |
| | 128,34 ppm ⎭ |
| | 68,48 ppm —CH$_2$— |
| | 21,51 ppm —CH$_3$ |
| $^1$H—NMR-spectrum (CDCl$_3$) | 8,54 ppm, s, 1 H, exchangeable for D$_2$O for —NH— |
| | 7,91/7,81/7,23/7,13 ppm, AB-Type 4 H for —C$_6$H$_4$—SO$_2$— |
| | 7,21 ppm, s, 5 H for —C$_6$H$_5$CH$_2$— |
| | 5,02 ppm, s, 2 H for —CH$_2$— |
| | 2,34 ppm, s, 3 H for —CH$_3$ |

EXAMPLE 3

Preparation of methane sulfonylisocyanate

A round flask with affixed packed column was charged with 44,56 g of methane sulfochloride (0,389 mol), 2 ml of TiCl$_4$ and 2 ml of SnCl$_4$ and heated to 120° C. in an oil bath. Subsequently 15 g of a total of 53,74 g of trimethyl silylisocyanate (0,466 mol) were added, whereby precipitation of a yellow-brown precipitate within the reaction mixture was observed. After the still temperature had dropped to 58° C. chlorotrimethyl silane was continually removed at the head at 58° to 60° C. until the bottom temperature had reached 135° C. The remaining portion of trimethyl silylisocyanate was then added portionwise in such a manner that a bottom temperature of 135° to 150° C. was maintained, while the chlorotrimethyl silane distilled at 50° to 60° C. The conversion was thus controlled for 9 hours, a bottom temperature of 160° C. in combination with a still temperature of 60° C. being registered.

As in example 2 the reaction mixture was first distilled through a Claisen-bridge under vacuum, by which process 31,80 g of a nearly colorless liquid of bp. (22 mbar) 73° to 80° C. were obtained. After rectification through a Vigreux-column 19,32 g of colorless methane sulfonylisocyanate, bp. (22 mbar) 79° to 81° C., were recovered, which according to gaschromatographic analysis still contained 6% methane sulfochloride.

Characterisation of methane sulfonylisocyanate

To 3,57 g of anhydrous benzyl alcohol (0,033 mol) in 50 ml absolute benzene 4,00 g methane sulfonyliscyanate (0,033 mol) were added dropwise within 5 minutes. Again a spontaneous exothermic reaction resulted. The benzene was evaporated leaving 7,61 g of a colorless, crystalline residue. After recristallisation from benzene/petrol ether 6,41 g N-benzyl oxycarbonyl methane sulfonamide, colorless crystals, fp. 111° to 112° C., were obtained.

Structure:

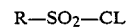

| IR-spectrum (KBr): | 3250 cm$^{-1}$ $\nu$(NH) |
| --- | --- |
| | 1750 cm$^{-1}$ $\nu$(C=O) |
| | 1345 cm$^{-1}$ $\nu$(SO$_2$)as |
| | 1155 cm$^{-1}$ $\nu$(SO$_2$)s |
| $^{13}$C—NMR-spectrum (acetone d$_6$) | 152,42 ppm C=O |
| | 136,41 ppm ⎫ |
| | 129,26 ppm ⎬ C$_6$H$_5$— |
| | 129,10 ppm ⎪ |
| | 128,83 ppm ⎭ |
| | 68,48 ppm —CH$_2$— |
| | 41,25 ppm CH$_3$— |
| $^1$H—NMR-spectrum (acetone d$_6$) | 9,98 ppm, s, 1 H, exchangeable for D$_2$O, for —NH— |
| | 7,37 ppm, s, 5 H for —C$_6$H$_5$— |
| | 5,20 ppm, s, 2 H for —CH$_2$— |
| | 3,25 ppm, s, 3 H for —CH$_3$. |

I claim:

1. A method of preparing sulfonyl isocyanates having the general formula

R—SO$_2$—NCO        I, wherein R is a linear or branched C$_1$- to C$_{18}$-alkyl radical, a phenyl radical, an alkyl phenyl radical having at least one linear or branched alkyl group containing from 1 to 18 C-atoms, or an isocyanate group, by reacting the corresponding sulfonylchlorides having the general formula

R—SO$_2$—CL        II, wherein R has the meaning as set forth above, with an isocyanate, characterized in that trimethyl silylisocyanate is used as the isocyanate and that the reaction is carried out in the presence of catalytic amounts of Lewis acids.

2. The method of claim 1 in which at least one halide having the formula $$AX_n \qquad \qquad III$$

is used as Lewis acid, wherein A represents an element selected from the group of boron, aluminum, titanium, tin, vanadium, antimony, iron or zinc, X is a halogen atom and n corresponds to the valence of A.

3. The method of claims 1 or 2, wherein the catalyst is used in an amount of about 0,1 to 20% by weight, based on the trimethyl silyl isocyanate.

4. The method of one of the claims 1 to 3, wherein the reaction is performed at a temperature of about 120° to 150° C.

5. The method of one of the claims 1 to 4, wherein the reaction is performed without a solvent and the trimethylchlorosilane formed is continuously removed from the reaction mixture.

6. The method of one of the claims 1 to 3, wherein the reaction is performed at a temperature of about 120° to 130° C.

* * * * *